US00PP17405P2

(12) United States Plant Patent
Winner

(10) Patent No.: US PP17,405 P2
(45) Date of Patent: Feb. 13, 2007

(54) ***COREOPSIS* PLANT NAMED 'BALCORSUNAY'**

(50) Latin Name: *Coreopsis grandiflora*
Varietal Denomination: Balcorsunay

(75) Inventor: Blair L. Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 107 days.

(21) Appl. No.: 11/296,685

(22) Filed: Dec. 7, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Audrey Charles

(57) ABSTRACT

A new and distinct cultivar of *Coreopsis* plant named 'Balcorsunay' characterized by its medium size golden-colored flowers, medium green-colored foliage, and vigorous, upright growth habit.

1 Drawing Sheet

Latin name of genus and species of plant claimed: *Coreopsis grandiflora.*
Variety denomination: 'Balcorsunay'.

BACKGROUND OF THE INVENTION

The present invention relates to a new and distinct cultivar of *Coreopsis* plant botanically known as *Coreopsis grandiflora* and hereinafter referred to by the cultivar name 'Balcorsunay'.

The new cultivar originated in a controlled breeding program in Santa Paula, Calif. during October 1999. The objective of the breeding program was the development of *Coreopsis* cultivars with large flowers, continuous flowering, and increased plant size.

The female (seed) parent of the new cultivar was the proprietary *Coreopsis grandiflora* breeding selection designated 62044-2, not patented, characterized its by single gold-colored flowers with a red base and mounded growth habit. The male (pollen) parent of the new cultivar was 'Walcoreop', U.S. Plant Pat. No. 10,299, characterized by its single gold-colored flowers and compact mounded growth habit. The new *Coreopsis* was discovered and selected by the inventor as a single flowering plant within the progeny of the above stated cross-pollination during August 2001 in a controlled environment at Santa Paula, Calif.

Asexual reproduction of the new cultivar by terminal stem cuttings since August 2001 at Santa Paula, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balcorsunay' as a new and distinct cultivar of *Coreopsis* plant:

1. Medium size golden-colored flowers;
2. Medium green-colored foliage; and
3. Vigorous, upright growth habit.

Plants of the new cultivar differ from plants of the female parent primarily in flower color and growth habit and from plants of the male parent primarily in growth habit.

Of the many commercially available *Coreopsis* cultivars known to the inventor, the most similar in comparison to the new cultivar is 'Walcoreop', U.S. Plant Pat. No. 10,299. However, in side by side comparisons, plants of the new cultivar differ from plants of 'Walcoreop' in the following characteristics:

1. Plants of the new cultivar have smaller inflorescences than plants of 'Walcoreop';
2. Plants of the new cultivar have more compact growth habit than plants of 'Walcoreop'; and
3. Plants of the new cultivar have flowers of a darker color than plants of 'Walcoreop'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcorsunay'. The plants were grown in 10 cm pots for 6 weeks in a greenhouse at West Chicago, Ill.

DETAILED BOTANICAL DESCRIPTION

Figure 1:
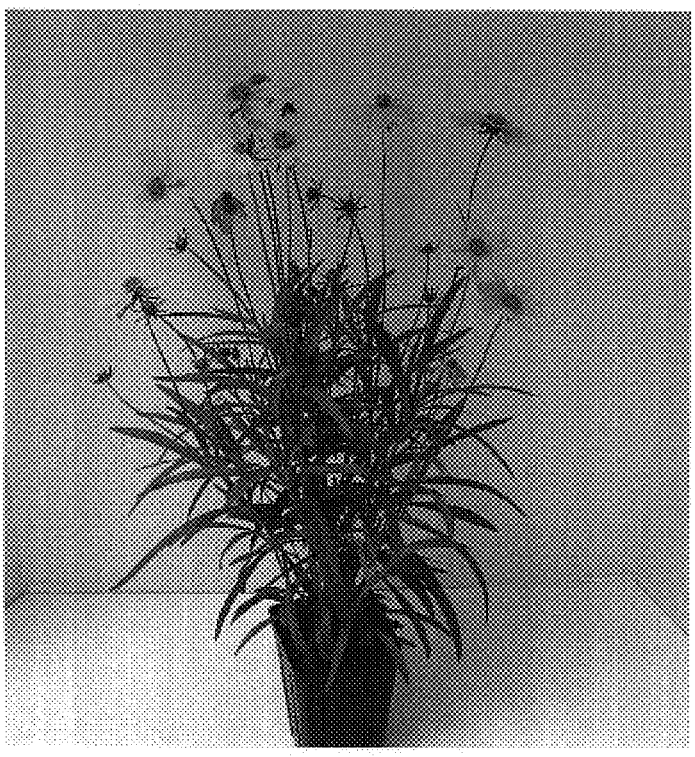
FIG. 1 illustrates a side view of the overall growth and flowering habit of 'Balcorsunay'.
Figure 2:
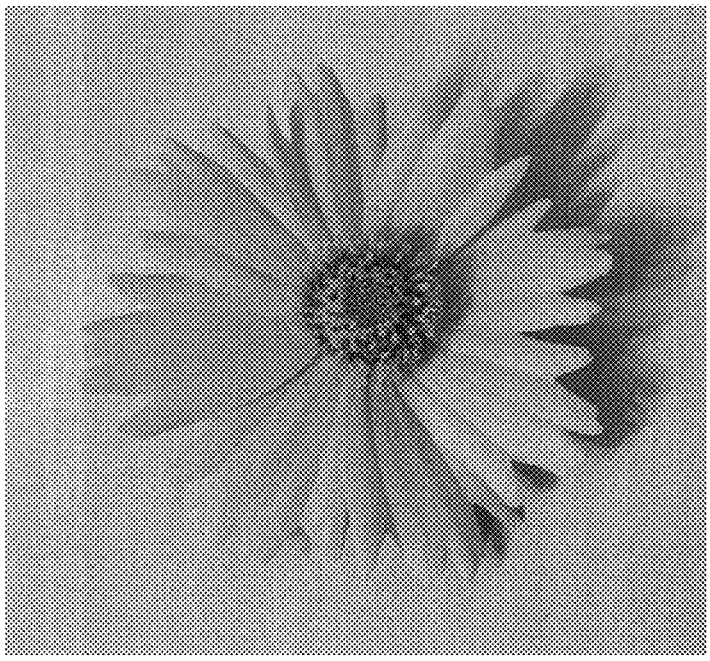
FIG. 2 illustrates a close-up view of an inflorescence of 'Balcorsunay' with all of the ray florets open and one-half of the disc florets open.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Aug. 24, 2005, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 6 weeks utilizing a soilless growth medium. Greenhouse temperatures were maintained at approximately 65° F. to 75° F. (18° C. to 24° C.) during the day and approximately 60° F. to 65° F. (15° C. to 18° C.) during the night. Greenhouse light levels of 6,000 to 9,000 footcandles were maintained during the day.

Botanical classification: *Coreopsis grandiflora* cultivar Balcorsunay.

Parentage:

*Female parent.*—Proprietary *Coreopsis grandiflora* breeding selection designated 62044-2, not patented.

*Male parent.*—'Walcoreop', U.S. Plant Pat. No. 10,299.

Propagation:

*Type cutting.*—Terminal stem.

*Time to initiate roots.*—Approximately 6 to 9 days.

*Time to produce a rooted cutting.*—Approximately 28 to 35 days.

*Root description.*—Fibrous.

*Rooting habit.*—Freely branching.

Plant description:

*Crop time.*—Approximately 6 to 9 weeks from a rooted cutting.

*Growth habit and general appearance.*—Perennial; vigorous, upright.

*Size.*—Height from soil level to top of plant plane: Approximately 45.3 cm. Width: Approximately 34.7 cm.

*Branching habit.*—Freely basal branching. Approximately 4 main branches per plant and lateral branches forming at every node.

*Branch.*—Strength: Strong. Shape: Square in cross section. Length: Approximately 14.3 cm. Diameter: Approximately 3.8 mm. Texture: Glabrous. Color: 143C. Internode length at center of branch: Approximately 4.2 cm.

*Foliage.*—Number of leaves per main branch: Approximately 11. Fragrance: None. Form: Simple. Arrangement: Opposite, sessile. Aspect: Perpendicular or obtuse angle to stem. Shape: Elliptic. Margin: Entire. Apex: Acute. Base: Attenuate. Venation pattern: Pinnate. Length of mature leaf: Approximately 11.0 cm. Width of mature leaf: Approximately 1.5 cm. Texture of upper and lower surfaces: Glabrous. Color of upper surface of mature foliage: 137A with venation of 144B. Color of lower surface of mature foliage: 137C with venation of 144B.

Flowering description:

*Flowering habit.*—'Balcorsunay' is freely flowering under growing conditions with substantially continuous blooming from late spring through autumn and year round in greenhouse environment.

*Time to first flower.*—Approximately 12 weeks from sticking of unrooted cutting.

*Lastingness of individual bloom.*—Approximately 10 to 14 days.

Inflorescence description:

*Type.*—Composite, daisy-like. Shape: Round. Diameter: Approximately 5.8 cm. Depth: Approximately 1.4 cm. Disc diameter: Approximately 1.4 cm. Disc and ray florets arranged acropetally on a capitulum. Aspect: Facing upward. Arrangement: Terminal, arising from leaf axils. Fragrance: None. Quantity per plant at 6 weeks: Approximately 6.

*Peduncle.*—Strength: Strong, flexible. Aspect: Erect. Length: Approximately 23.5 cm. Diameter: Approximately 1.7 mm. Texture: Pubescent with very sparse short hairs. Color: Darker than 144A.

*Bud rate of opening.*—Generally takes 1 to 2 days for bud to progress from first color to fully open flower.

*Bud just before opening.*—Shape: Spherical. Length just before color: Approximately 9.7 mm. Diameter just before color: Approximately 9.3 mm. Length at first color: Approximately 1.3 mm. Diameter at first color: Approximately 1.1 mm. Texture just before and at first color: Glabrous. Color: Closest to 163B.

*Ray florets.*—Quantity: Approximately: 8. Arrangement: In two whorls. Aspect: Flat. Shape: Obovate. Apex: Emarginate with four tips. Base: Truncate. Margin: Entire. Length: Approximately 2.5 cm. Width: Approximately 1.9 cm. Texture of upper and lower surfaces: Glabrous. Color of upper surface of fully open floret: Closest to 17A. Color of lower surface of fully open floret: Closest to 14A.

*Disc florets.*—Quantity: Approximately: 139. Arrangement: Massed at the center of the inflorescence. Aspect: Erect. Shape: Tubular. Apex: Five acute tips. Base: Attenuate, fused. Margin: Entire. Length: Approximately 7.3 mm. Diameter at apex: Approximately 2.0 mm. Diameter at base: Approximately 0.8 mm. Texture of upper and lower surfaces: Glabrous. Color of upper and lower surfaces unopened and fully opened: Closest to 17A.

*Receptacle.*—Shape: Disc. Height: Approximately 1.9 mm. Diameter: Approximately 5.7 mm. Color: 145D.

*Sepals.*—Quantity: 8. Arrangement: Non-imbricate. Shape: Lanceolate. Aspect: Perpendicular to stem. Length: Approximately 1.5 cm. Width: Approximately 2.9 mm. Texture: Glabrous. Color: 137C.

*Phyllaries.*—Quantity: 8. Arrangement: Overlapping at base. Shape: Linear. Apex: Acute. Margin: Entire. Base: Truncate. Length: Approximately 1.3 cm. Width: Approximately 3.7 mm. Texture of upper and lower surfaces: Glabrous. Color of upper and lower surfaces: Darker than 144A.

*Reproductive organs.*—Androecium: On disc florets only: Stamen quantity: 5. Anther shape: Linear. Anther length: Approximately 2.8 mm. Anther color: 13A. Pollen amount: Abundant. Pollen color 14A. Gynoecium: On disc and ray florets: Pistil quantity: One per floret. Pistil length: Approximately 9.0 mm. Stigma shape: Two branched. Stigma length: Approximately 1.0 mm. Stigma color: 13B. Style length: Approximately 8.0 mm. Style color: 13C at distal end, 13D at proximal end. Ovary length: Approximately 3.0 mm. Ovary color: Between 150C and 150D.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Balcorsunay', substantially as herein shown and described.

* * * * *